US012702859B1

(12) United States Patent
Hanks et al.

(10) Patent No.: US 12,702,859 B1
(45) Date of Patent: Aug. 11, 2026

(54) DUAL PATCH SYSTEM FOR MEASURING TISSUE PROPERTIES

(71) Applicants: John Hanks, Austin, TX (US); Amir Zavareh, College Station, TX (US)

(72) Inventors: John Hanks, Austin, TX (US); Amir Zavareh, College Station, TX (US)

( * ) Notice: Subject to any disclaimer, the term of this patent is extended or adjusted under 35 U.S.C. 154(b) by 0 days.

(21) Appl. No.: 19/303,229

(22) Filed: Aug. 18, 2025

(51) Int. Cl.

| | |
|---|---|
| ***A61N 5/06*** | (2006.01) |
| ***A61N 1/36*** | (2006.01) |
| ***G16H 20/40*** | (2018.01) |
| ***G16H 40/67*** | (2018.01) |
| ***G16H 50/20*** | (2018.01) |

(52) U.S. Cl.
CPC ....... *A61N 5/0616* (2013.01); *A61N 1/36031* (2017.08); *G16H 20/40* (2018.01); *G16H 40/67* (2018.01); *G16H 50/20* (2018.01); *A61N 2005/0645* (2013.01); *A61N 2005/0651* (2013.01); *A61N 2005/0659* (2013.01); *A61N 2005/0663* (2013.01)

(58) Field of Classification Search
CPC .............. A61N 5/0616; A61N 1/36031; A61N 2005/0645; A61N 2005/0651; A61N 2005/0659; A61N 2005/0663; G16H 20/40; G16H 40/67; G16H 50/20
USPC ................ 607/50, 2, 88, 89; 600/323; 606/9
See application file for complete search history.

(56) References Cited

U.S. PATENT DOCUMENTS

| | | | | |
|---|---|---|---|---|
| 9,672,471 | B2 * | 6/2017 | Boyden | G06N 20/00 |
| 11,857,294 | B2 * | 1/2024 | Hanks | A61B 5/7275 |
| 2007/0129776 | A1 * | 6/2007 | Robins | A61N 5/0613 607/88 |
| 2011/0263950 | A1 * | 10/2011 | Larson | A61B 5/0205 600/595 |
| 2019/0083809 | A1 * | 3/2019 | Zhang | A61N 5/0616 |
| 2021/0402212 | A1 * | 12/2021 | Schupp | A61N 5/067 |
| 2022/0203112 | A1 * | 6/2022 | Iger | A61N 1/328 |
| 2022/0233135 | A1 * | 7/2022 | Shelton, IV | A61B 5/0531 |

* cited by examiner

*Primary Examiner* — Carl H Layno
*Assistant Examiner* — Mary Grace Schlueter
(74) *Attorney, Agent, or Firm* — Benjamin Aaron Adler

(57) ABSTRACT

Provided herein are medical patches and dual patch systems for real-time post-operative monitoring of tissue properties and flap monitoring. The medical patch may be a flap patch that has modules to measure tissue oxygenation and skin temperature and to deliver a therapy to the tissue and to control the flap patch or may be a reference patch configured to also measure ambient temperature. Both the flap patch and the reference patch additionally may be configured to detect edema. The dual patch system has the flap patch, a reference patch and a reference module. Also provided is a method for real-time monitoring and modulating tissue health in a surgical flap via the dual patch system.

17 Claims, 7 Drawing Sheets

DUAL PATCH SYSTEM FOR MEASURING TISSUE PROPERTIES

BACKGROUND OF THE INVENTION

Field of the Invention

The present invention relates to the field of medical patch systems and tissue reconstruction. More particularly, the present invention relates to a wireless dual patch system for combined remote monitoring of relative flap and healthy tissue in real-time to measure tissue properties.

Description of the Related Art

For the past several decades, there have been unprecedented advances in microsurgery and tissue reconstruction (1,2). Despite these advances, flap failures are still common due to the inability to accurately monitor flap health that might deteriorate by both vascular occlusions and surgical site infections (SSIs). More than 95% of flap failures occur within 72 h of surgery. The costliest failures occur at later stages, after the patients have been discharged from the hospital, when they don't have access to emergency medical care. Apart from being an economic burden, flap failures due to vascular occlusions or surgical site infections can be complex and traumatic to the patients (3,4).

Currently tissue flap health is monitored by tissue oxygen saturation (StO2) only. However, a decrease in surface temperature is symptomatic of tissue ischemia and indicates obstruction earlier than a drop in StO2 (5). Prior research has shown that a temperature difference between the flap tissue and surrounding skin >4.5° C. is indicative of infection and flap failure (6), which requires immediate action (7). In addition, the symptoms for surgical site infections appear 3-7 days post operatively (8) after the patient has been discharged, and >96% of surgical site infections were identified at readmission when the flap salvage was impossible (9). Surgical site edema is also indicative of transplant rejection, vascular obstruction, and infection, which is not currently monitored in surgical flaps (8). Moreover, current post-operative monitoring techniques involve wired devices that are tethered to a stationary computer and display that require the patients to stay in the hospital, which can present significant patient compliance issues and incur additional medical costs. There is no single device available that allows measurement of all the above markers of tissue health.

Thus the art is deficient in wireless patch technology that sends patient data to a HIPAA-compliant cloud server whereby patients can be monitored directly from home by their healthcare providers. Specifically, the prior art is deficienct in a dual patch system to measure temperature, edema and StO2 in a post-operative patient with a flap reconstruction and wirelessly transmit the acquired data. The present invention fulfills this long-standing need and desire in the art.

SUMMARY OF THE INVENTION

The present invention is directed to a medical patch for monitoring tissue properties in a patient. The medical patch comprises a first module configured to measure tissue oxygenation, a second module configured to measure skin temperature (T), a third module configured to deliver a therapy effective to accelerate healing of tissue and to stimulate cell proliferation therein, and a control module. The control module is configured to power the medical patch, to receive wirelessly multimodal time-synchronized data comprising tissue oxygenation and skin temperature data, to calculate at least one differential physiological parameter based on the time-synchronized data, to execute an AI algorithm trained to classify a tissue viability state and predict an ischemic risk based on a series of the multimodal time-synchronized data, to issue alerts if the ischemia risk exceeds a defined threshold, and to adjust dynamically parameters of the therapy delivered by the third module in response to the tissue viability state and ischemic risk.

In a related medical patch, the second module is further configured to measure ambient temperature. Another related medical patch further comprises a fourth module configured to detect edema in tissue.

The present invention also is directed to a dual patch system for post-operative flap monitoring. The system comprises a flap patch removably attachable to a surgical flap, a reference patch removably attachable to healthy tissue adjacent to the surgical flap and a control module. In the flap patch a first tissue oxidation module is configured to monitor and measure StO2, where the tissue oxidation module has a plurality of surface-mounted LEDs that emit at a combination of different wavelengths and at least one photodetector. A first thermal sensing module comprises at least one skin-contact temperature sensor and a therapeutic excitation module comprises a photobiomodulation patch with a driver circuit or a cathode and anode, each of which is configured to accelerate healing and stimulate cell proliferation in the surgical flap. The reference patch comprises a second tissue oxidation module configured as the first oxidation module and a second thermal sensing module that comprises at least one skin-contact temperature sensor and an ambient temperature sensor. The control module is configured to power the flap patch and the reference patch, to receive wirelessly multimodal time-synchronized data from the flap patch and the reference patch comprising tissue oxygenation and skin temperature data, to calculate at least one differential physiological parameter based on the time-synchronized data, to execute an AI algorithm trained to classify a tissue viability state and predict an ischemic risk based on a series of the multimodal time-synchronized data from the flap patch, to issue alerts locally and to a cloud-based dashboard if the ischemic risk exceeds a defined threshold, and, to adjust dynamically parameters of the therapy delivered by the third module in response to the tissue viability state and ischemic risk.

In a related dual patch system, the flap patch and the reference patch further comprise an edema detection module that has a plurality of LEDs that emit light with center wavelengths of about 900 nm to about 1000 nm, of about 1400 nm to about 1500 nm or about 1800 nm to about 2200 nm.

The present invention is directed further to a method for real-time monitoring and modulating tissue health in a surgical flap. In this method, the flap patch and the reference patch of the dual patch system described herein are placed onto the surgical flap and onto the healthy tissue adjacent adjacent to the flap patch. Temperature data and tissue oxygenation (StO2) data are acquired continuously from the flap patch and the reference patch and physiological deltas are computed between the surgical flap and the healthy tissue. Multimodal time-series data is inputted into an AI algorithm to determine a predicted risk level of tissue viability in the surgical flap and parameters of the photobiomodulation patch in the flap patch are adjusted automatically in response to the predicted risk level. Wireless alerts are issued to a health provider if a deterioration in flap health is detected or predicted.

Other and further aspects, features, benefits, and advantages of the present invention will be apparent from the following description of the presently preferred embodiments of the invention given for the purpose of disclosure.

BRIEF DESCRIPTION OF THE FIGURES

The appended drawings have been included herein so that the above-recited features, advantages, and objects of the invention will become clear and can be understood in detail. These drawings form a part of the specification. It is to be noted, however, that the appended drawings illustrate preferred embodiments of the invention and should not be considered to limit the scope of the invention.

FIG. 1A shows the flap patch and reference patch illustrating for each the StO2 measurement module, the temperature measurement module and a photobiomodulation patch. FIG. 1B shows the patch system of FIG. 1A with an edema measurement unit.

FIG. 2A shows the flap patch and reference patch illustrating for each the StO2 measurement module, the temperature measurement module and a cathode and an anode for electrical stimulation of tissue. FIG. 2B shows the patch system of FIG. 2A with an edema measurement module.

FIG. 4A shows the predicted error and FIG. 4B shows the predicted StO2.

DETAILED DESCRIPTION OF THE INVENTION

Figure 1A:
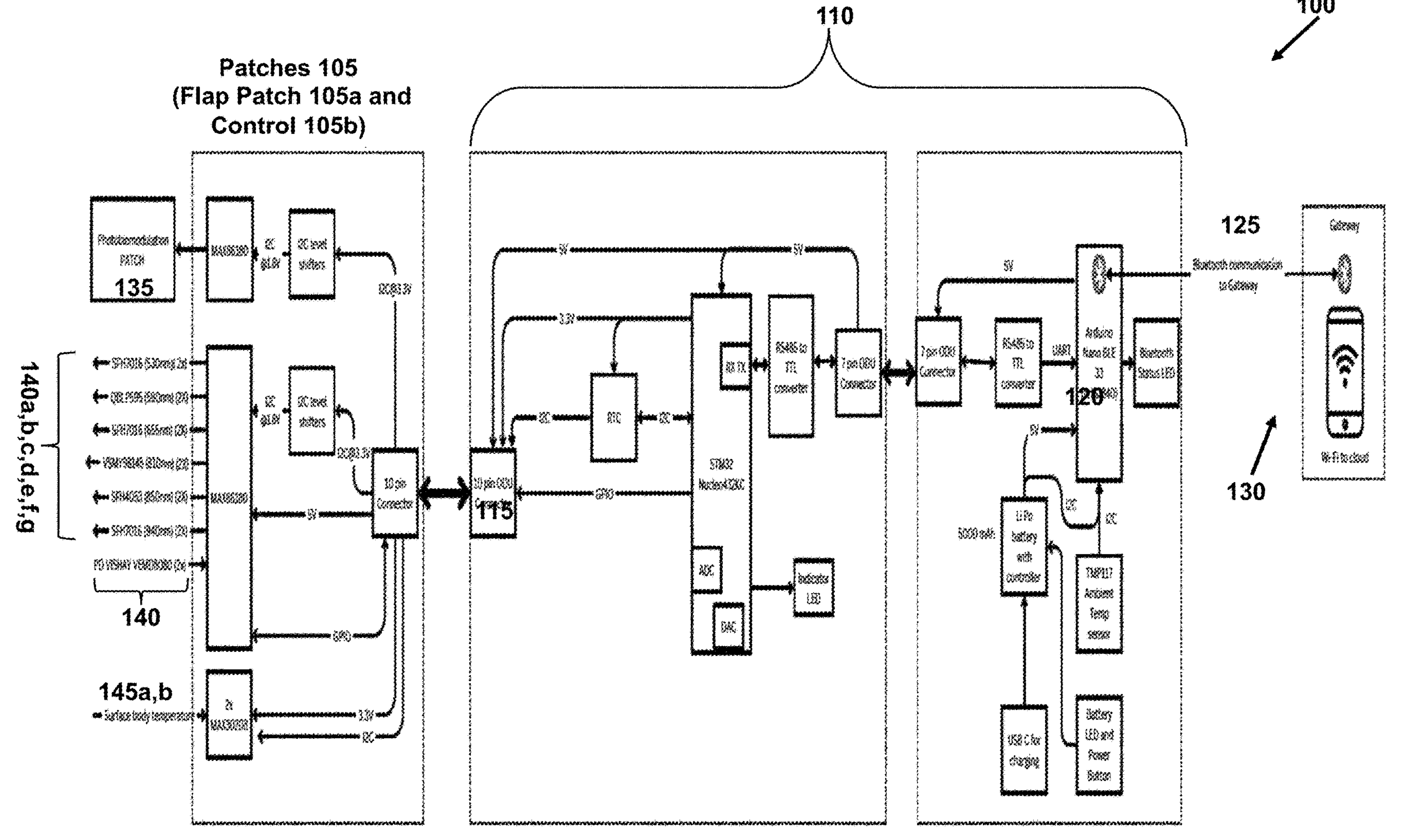
FIGS. 1A-1B are schematics of an embodiment of the wireless dual patch system.

As used herein, the term “a” or “an” when used in conjunction with the term “comprising” in the claims and/or the specification may mean “one,” but it is also consistent with the meaning of “one or more,” “at least one,” and “one or more than one.” Some embodiments of the invention may consist of or consist essentially of one or more elements, method steps, and/or methods of the invention. It is contemplated that any method described herein can be implemented with respect to any other method described herein.

As used herein, the term “or” in the claims is used to mean “and/or” unless explicitly indicated to refer to alternatives only or the alternatives are mutually exclusive, although the disclosure supports a definition that refers to only alternatives and “and/or.”

As used herein, “comprise” and its variations, such as “comprises” and “comprising,” is understood to imply the inclusion of a stated item, element or step or group of items, elements or steps but not the exclusion of any other item, element or step or group of items, elements or steps unless the context requires otherwise. Similarly, “another” or “other” may mean at least a second or more of the same or different claim element or components thereof.

As used herein, the term “about” refers to a numeric value, including, for example, whole numbers, fractions, and percentages, whether or not explicitly indicated. The term “about” generally refers to a range of numerical values (e.g., ±5-10% of the recited value) that one of ordinary skill in the art would consider equivalent to the recited value (e.g., having the same function or result). In some instances, the term “about” may include numerical values that are rounded to the nearest significant figure.

As used herein, the ordinal adjectives “first” and“second” unless otherwise specified are used to describe a common object, merely indicate that different instances of like objects are being referred to, and are not intended to imply that the objects so described must be in a given sequence, either temporally, spatially, in ranking, or in any other manner.

As used herein, the terms “subject” and “patient” are interchangeable and refer to any individual on which any of the medical devices described herein are used.

In one embodiment of the present invention, there is provided a medical patch for monitoring tissue properties in a patient, comprising a first module configured to measure tissue oxygenation; a second module configured to measure skin temperature; a third module configured to deliver a therapy effective to accelerate healing of tissue and to stimulate cell proliferation therein; and a control module configured to power the medical patch; receive wirelessly multimodal time-synchronized data comprising tissue oxygenation and skin temperature data; calculate at least one differential physiological parameter based on the time-synchronized data; execute an AI algorithm trained to classify a tissue viability state and predict an ischemic risk based on a series of the multimodal time-synchronized data; to issue alerts if the ischemia risk exceeds a defined threshold; and adjust dynamically parameters of the therapy delivered by the third module in response to the tissue viability state and ischemic risk.

Further to this embodiment, the medical patch comprises a fourth module configured to detect edema in tissue. In this further embodiment, the fourth module may comprise another plurality of LEDs that emit light with center wavelengths of about 900 nm to about 1000 nm, of about 1400 nm to about 1500 nm or about 1800 nm to about 2200 nm to detect the edema.

In both embodiments, the first module may comprise a plurality of LEDs that emit at 625 nm, 660 nm, 805 nm, and 870 nm dynamically selectable in combinations based on a tissue reflectance. Also in both embodiments the second module may be further configured to measure ambient temperature. Particularly, in this embodiment the medical patch may be a reference patch positionable on healthy tissue.

Also in both embodiments, the third module may deliver a photobiomodulation therapy or an electrical stimulation therapy. In one aspect, the third module may comprise a plurality of LEDs that emit red light with at least one wavelength of about 600 nm to about 1100 nm, effective for a controlled photobiomodulation, and a driver circuit. In another aspect, the third module may comprise a cathode and an anode effective to deliver an electric current of about 0 mA to about 30 mA, a frequence of 0 KHz to about 1 KHz, and duty cycles of 0% to 100% with different shapes to pass through post-operative tissue. In addition, the control module may be configured to calculate differential physiological parameter is ΔStO2 or ΔTor a combination thereof. Furthermore, the medical patch may be a flap patch positionable on post-operative flap tissue.

In another embodiment of the present invention, there is provided a dual patch system for post-operative flap monitoring, comprising a flap patch removably attachable to a surgical flap and comprising a first tissue oxidation module configured to monitor and measure StO2, the tissue oxidation module having a plurality of surface-mounted LEDs that emit at a combination of different wavelengths and at least one photodetector; a first thermal sensing module comprising at least one skin-contact temperature sensor; and a therapeutic excitation module comprising a photobiomodulation patch with a driver circuit or a cathode and anode, each of which is configured to accelerate healing and stimulate cell proliferation in the surgical flap; a reference patch removably attachable to healthy tissue adjacent to the surgical flap and comprising a second tissue oxidation module configured to monitor and measure StO2, said tissue oxidation module having a plurality of surface-mounted LEDs that emit at a combination of different wavelengths and at least one photodetector; a second thermal sensing module comprising at least one skin-contact temperature sensor and an ambient temperature sensor; and a control module configured to power the flap patch and the reference patch; receive wirelessly multimodal time-synchronized data from the flap patch and the reference patch comprising tissue oxygenation and skin temperature data; calculate at least one differential physiological parameter based on the time-synchronized data; execute an AI algorithm trained to classify a tissue viability state and predict an ischemic risk based on a series of the multimodal time-synchronized data from the flap patch; to issue alerts locally and to a cloud-based dashboard if the ischemic risk exceeds a defined threshold; and adjust dynamically parameters of the therapy delivered by the third module in response to the tissue viability state and ischemic risk.

Further to this embodiment, the flap patch and the reference patch comprise an edema detection module that has a plurality of LEDs that emit light with center wavelengths of about 900 nm to about 1000 nm, of about 1400 nm to about 1500 nm or about 1800 nm to about 2200 nm.

In both embodiments, the plurality of surface-mounted LEDs in the first tissue oxidation module and the second tissue oxidation module may emit at 625 nm, 660 nm, 805 nm, and 870 nm. In one aspect of both embodiments, the photobiomodulation patch in the flap patch may comprise a plurality of LEDs that emit red light with at least one wavelength of about 600 nm to about 1100 nm effective to control photobiomodulation. In another aspect, the cathode and anode in the flap patch may be effective to deliver an electric current of about 0 mA to about 30 mA, a frequence of 0 KHz to about 1 KHz, and duty cycles of 0% to 100% with different shapes to pass through post-operative tissue.

Also in both embodiments and aspects thereof, the AI algorithm is a deep recurrent neural network trained on labeled flap outcome data to predict the probability of flap compromise within a 6-hour horizon. Particularly, the AI algorithm comprising attention-based temporal filtering configured to weigh recent versus historical measurements in a prediction process.

In yet another embodiment of the present invention, there is provided a method for real-time monitoring and modulating tissue health in a surgical flap, comprising the steps of placing the flap patch and the reference patch of the dual patch system of claim 12 onto the surgical flap and onto the healthy tissue adjacent adjacent to the flap patch; acquiring continuously temperature data and tissue oxygenation (StO2) data from the flap patch and the reference patch; computing physiological deltas between the surgical flap and the healthy tissue; inputting multimodal time-series data into an AI algorithm to determine a predicted risk level of tissue viability in the surgical flap; adjusting automatically parameters of the photobiomodulation patch in the flap patch in response to the predicted risk level; and issuing wireless alerts to a health provider if a deterioration in flap health is detected or predicted.

In this embodiment, the AI algorithm may be a deep neural network, the method comprising training the AI algorithm on labeled flap outcome data to predict the probability of flap compromise within a 6-hour horizon, said AI algorithm comprising attention-based temporal filtering configured to weigh recent versus historical measurements in a prediction process.

Provided herein are a wireless, low-cost, at home monitoring system that measures tissue properties of the flap and adjacent healthy tissue to monitor flap health. Particularly, provided are wireless dual patch systems for combined real-time remote monitoring of relative tissue temperature (T) and tissue oxygenation (StO2), and means for biomodulation to promote and accelerate healing, for example, via photobiomodulation or electrical stimulation. Alternatively, the system may also comprise an edema detector for each patch which is monitored by the system.

The system requires two patches, i.e., one on the transplanted flap called the flap patch and another on adjacent healthy tissue called the reference patch. The proposed dual patch system ensures meticulous monitoring of flap health, since it can simultaneously measure multiple markers of flap health, such as relative temperature between the flap and the adjacent tissue, StO2 and edema. The system utilizes BLUETOOTH (Bluetooth SIG, Inc.) and AI algorithms to dynamically, in real time record, calculate and transmit monitored values to a smart device, a computer and/or to a cloud server, such as a HIPAA-compliant cloud server in view of the personal, medical nature of the transmitted information.

Disruption of perfusion to a flap may result in flap necrosis and tissue loss from ischemia. If blood supply is low, the blood pulse to the flap may also be minimal. Timely post-operative, remote monitoring of flap health enables identification of possible vascular occlusions and infections. The collection and transmission of data to a HIPAA-compliant cloud server is performed in real-time for 10 sec. every 5 minutes, and alert the patients/doctors in case of any alarming or abnormal values, thus enabling swift medical attention well before flap failure occurs. The flap failure rate is decreased thereby reducing the cost of flap salvage procedures. Thus, provided herein are methods for remote monitoring a patient's post-operative recovery and flap health.

Particular embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1 is a schematic of one embodiment of the wireless dual patch system 100 representing as 105 both the flap patch **105*a* to be positioned on the post-operative flap tissue and a reference patch 105*b* to be positioned on a post-operative healthy tissue, reference tissue or adjacent tissue both enabling StO2 measurement, temperature monitoring, and photobiomodulation. A single hub or control module 110 comprising a microcontroller 115 controls both patches, power thereto and an arduino 120 configured to receive data from various modules, units and sensors and sends the data via BLUETOOTH connectivity 125 to a receiver/display device 130**, such as a smart phone and/or cloud server, for example, a HIPAA-compliant cloud server. The patches have flexible printed circuit boards (FPCB) thereby enabling contouring around the flap tissue and the healthy tissue for improved signal acquisition and onboard preprocessing circuits to normalize and denoise signals prior to wireless transmission to the receiver/display device. For example, photoplethysmographic signals may be denoised.

The flap patch is connected to a therapeutic excitation module such as a photobiomodulation patch 135 configured to accelerate or increase tissue healing and to stimulate cell proliferation in the tissue flap. The therapeutic excitation module is configured to utilize red light with a wavelength of about 600 nm to about 1100 nm. This enables controlled photobiomodulation. The therapeutic excitation module includes a driver circuit that modulates the pulse width and frequency of the red light based on AI-detected ischemic trends.

The flap patch has a tissue oxygenation module 140 with a plurality of LEDs emitting at different wavelengths 140*a, b, c, d, e, f* and at least one photodetector 140*g*. *The tissue oxygenation module has LEDs that emit at least at* 625 nm, 660 nm, 805 nm, and 870 nm. The module is configured to dynamically select combinations of wavelengths based on tissue reflectance. The flap patch and the reference patch each have a thermal sensing module 145*a,b* where each include at least one skin-contact module. The reference patch also has an ambient temperature sensor.

The control module is configured to wirelessly receive time-synchronized tissue oxygenation data and temperature data from both the flap patch and/or the reference patch and to receive ambient temperature data from the reference patch. The control module is configured to calculate differential physiological parameters, for example, but not limited to, ΔTemp (T) and $\Delta StO_2$. The control module is configured to execute an AI algorithm or model trained to classify tissue viability state and forecast ischemic risk based on multi-modal time-series data and to dynamically adjust the intensity and duty cycle of the red light therapy module in the flap patch in response to real-time classification or trend analysis outcomes.

The AI model may be a deep recurrent neural network trained on labeled flap outcome data to predict the probability of flap compromise within a 6-hour horizon. The AI model is configured for attention-based temporal filtering to weigh recent versus historical measurements in the prediction process. The control module issues alerts locally and to a cloud-based dashboard if predicted ischemia probability exceeds a defined threshold.

Figure 1B:
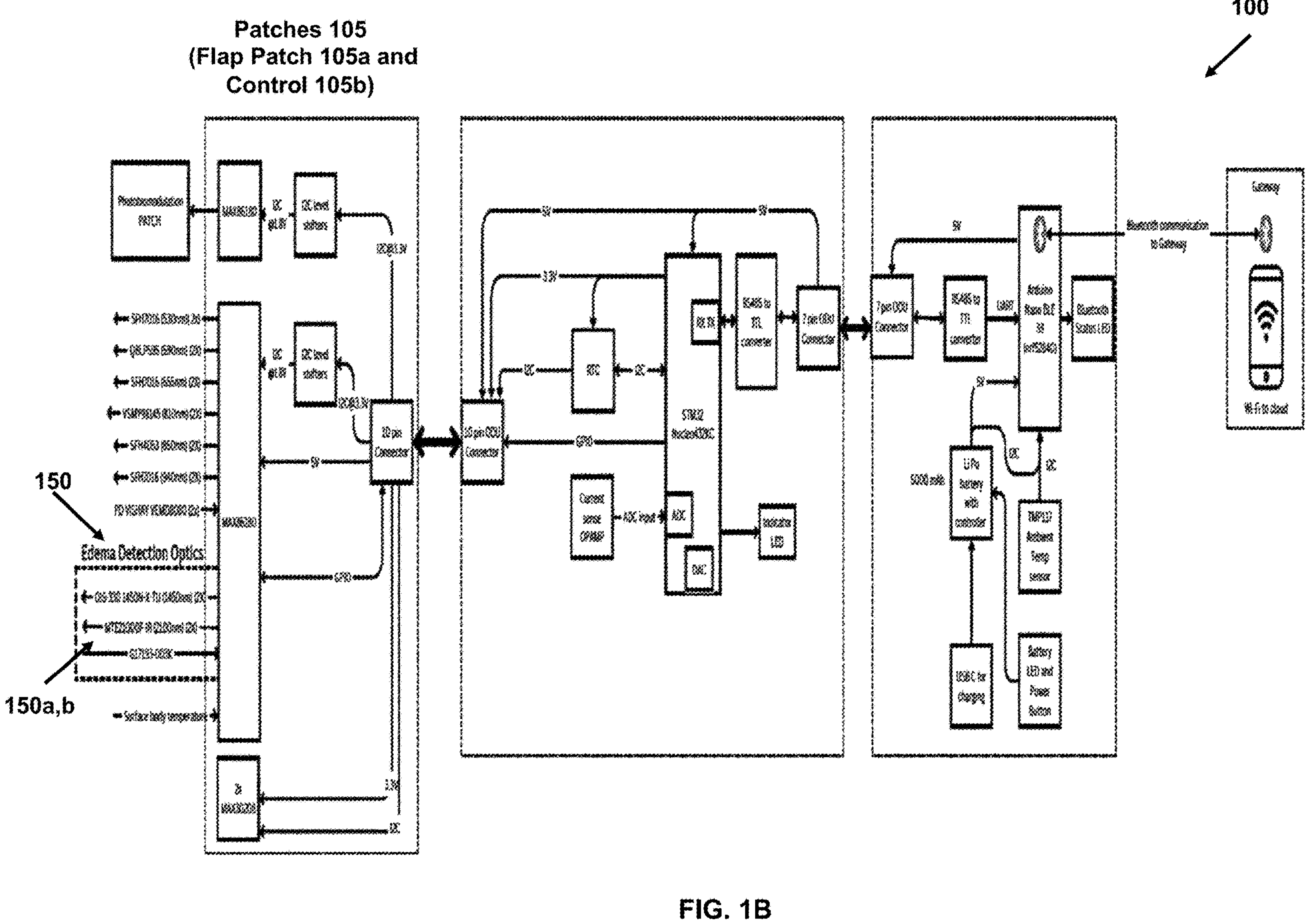

With continued reference to FIG. 1A, FIG. 1B is a schematic of the wireless dual patch system 100 plus an edema detection unit 150 configured to detect edema via optical means in the short wave infrared wavelength (900 nm-2500 nm) (100) range. The flap patch or the reference patch or both has edema detection optics 150*a,b* that utilize additional LEDs to detect, via at least one photodetector, edema in the flap tissue and/or the healthy tissue. The LEDs emit light with center wavelengths in the range of about 900 nm to 1000 nm, about 1440 nm to about 1500 nm or about 1800 nm to about 2200 nm. Preferably, the wavelengths are about 1400 nm or 2100 nm.

Figure 2A:
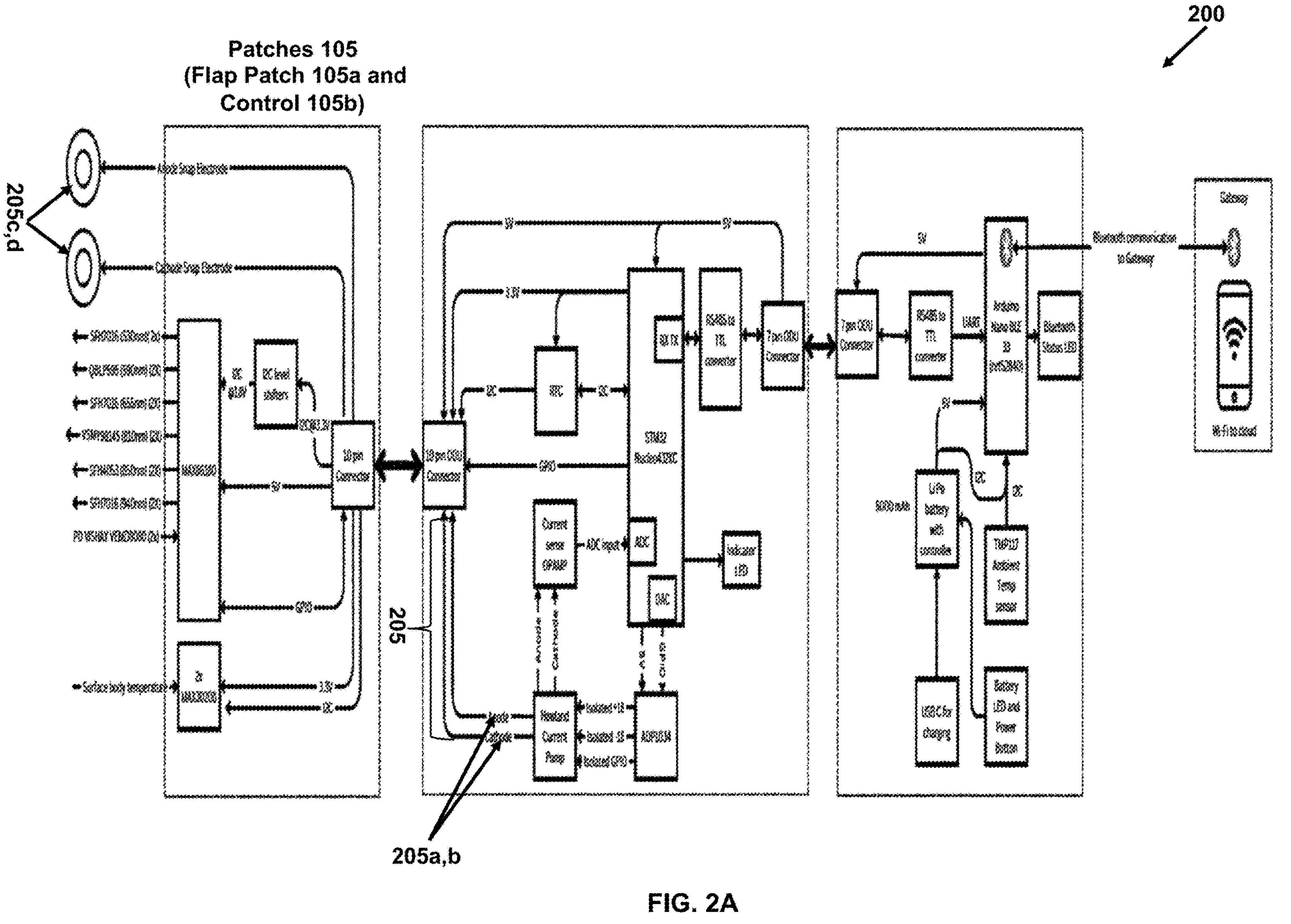
FIGS. 2A-2B are schematics of another embodiment of the wireless dual patch system.

With continued reference to FIG. 1A, FIG. 2A is a schematic of a related embodiment of the wireless dual patch system 200. This system 200 is identical to the wireless dual patch system 100 except that the therapeutic excitation module is replaced with a means of electrical stimulation 205 comprising a cathode 205*a* and anode 205*b* in the control module whereby the delivery of the electrical stimulation is represented at 205*c,d*. The therapeutic excitation module utilizes an electrical microcurrent from 0 mA to about 30 mA, a frequency from 0 KHz to about 1 KHz, duty cycles from 0 to 100 and different shapes. The module is configured to send the electrical current across the surgical site of the flap tissue or adjacent tissue.

Figure 2B:
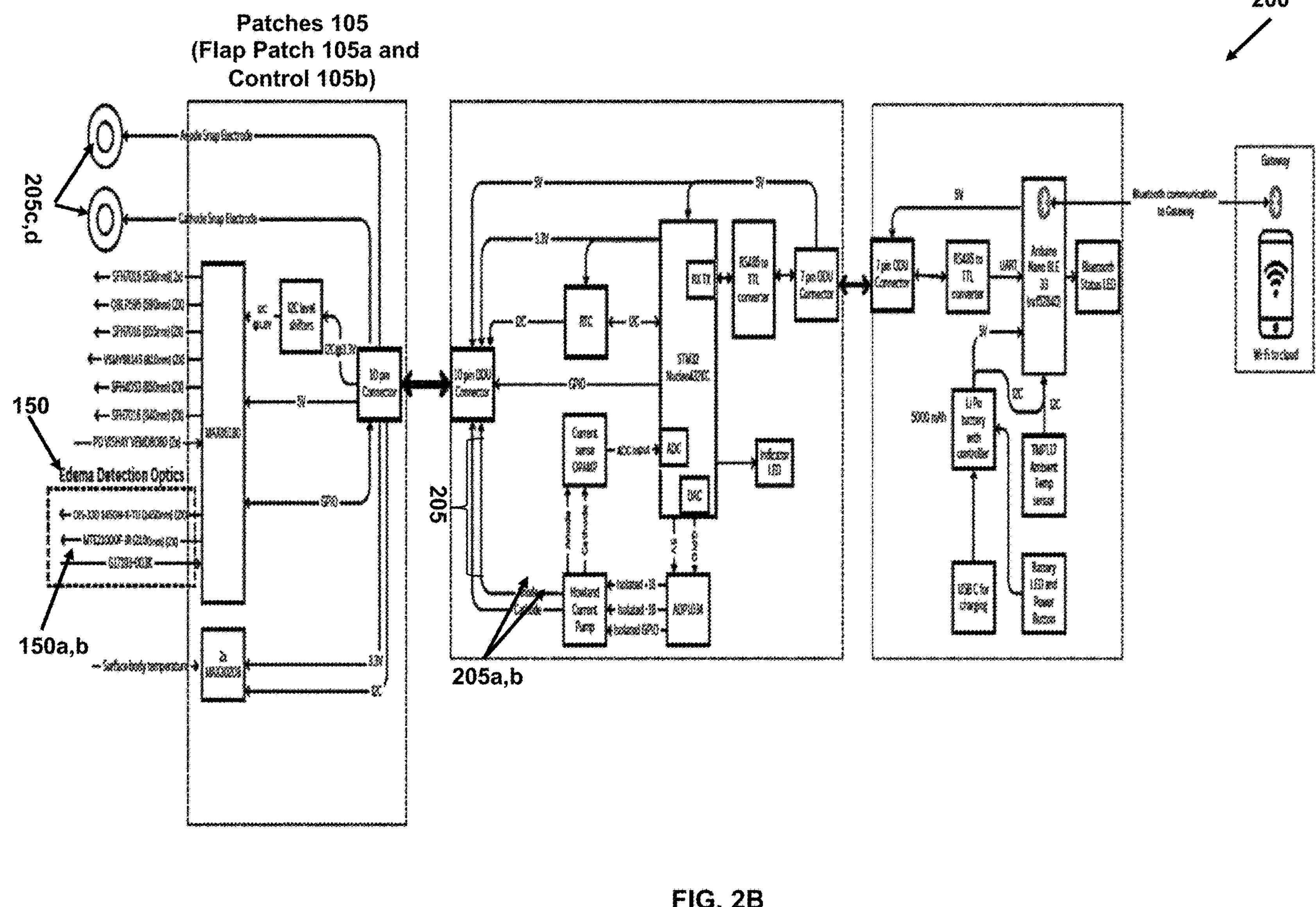

With continued reference to FIG. 2A, FIG. 2B is a schematic of the wireless dual patch system 200 plus an edema detection unit 150 configured to detect edema via the detection optics 150*a,b* as described in FIG. 1B.

Figure 3:
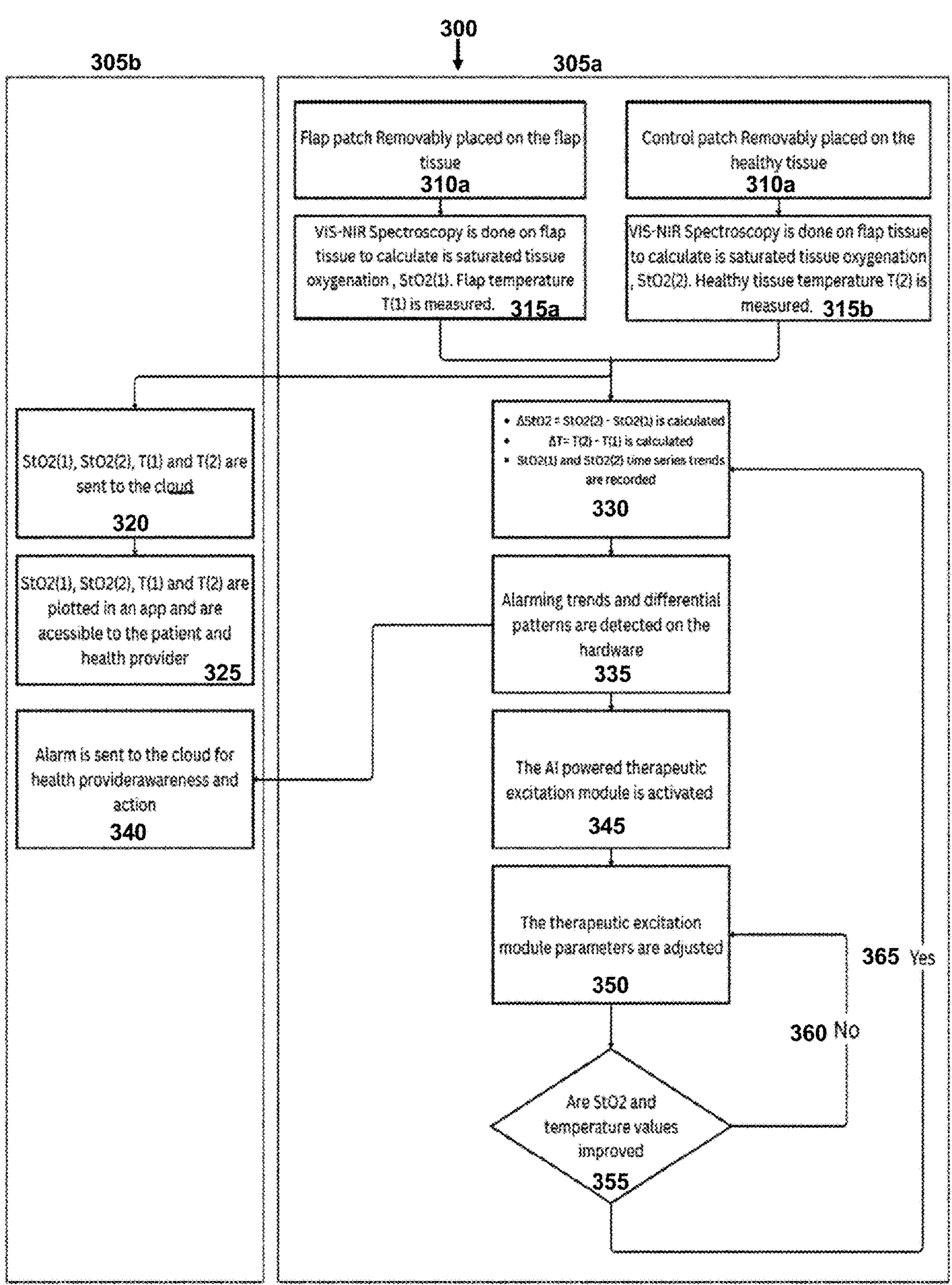
FIG. 3 is a flowchart of the hardware and software functions of the wireless dual patch system.

FIG. 3 is a flowchart 300 illustrating the operation of the hardware 305*a* and software 305*b* components of the wireless dual patch system to measure and to calculate tissue oxygenation and tissue temperature values for flap tissue and healthy tissue, to send the determined values to the cloud, to power and to activate the therapeutic excitation module, and to reassess the tissue oxygenation and tissue temperature values after delivery of the therapeutic stimulation. Particularly, the flap patch and the reference patch are removably placed on the flap tissue and the healthy tissue at 310*a,b*, respectively. The flap tissue saturated tissue oxygenation, StO2(1), and the healthy tissue saturated tissue oxygenation, StO2(2), are calculated via VIS-NIR spectroscopy and the flap temperature T(1) and healthy tissue temperature T(2) are measured at 315*a,b*. StO2(1), StO2(2), T(1) and T(2) values are sent to the cloud at 320 and plotted in an app which is accessible to both the patient and health provider at 325.

At 330 the differential physiological parameters ΔStO2=StO2(2)−StO2(1) and ΔT=T(2)−T(1) are calculated and StO(1) and StO(2) and T(1) and T(2) time series trends are recorded. If alarming trends and differential patterns are detected on the hardware at 335, then at 340 an alarm is sent to the cloud to alert the health provider. Also, in addition to sending the alarm the AI powered therapeutic module is activated at 345 and the therapeutic excitation module parameters are adjusted at 350. After therapeutic stimulation of the flap tissue and healthy tissue, the StO2 and temperature values are checked for improvement at 355. If no improvement 360 is found, the therapeutic excitation parameters are readjusted at 350. If improvement 365 in the values is found, then the ΔStO2=StO2(2)−StO2(1) and ΔT=T(2)−T(1) calculations are made and T(1) and T(2) time series trends recorded on the improved values at 330.

The following examples are given for the purpose of illustrating various embodiments of the invention and are not meant to limit the present invention in any fashion.

Example 1

Testing of Patch Efficacy
In Vivo StO2 Measurement

Figure 4A:
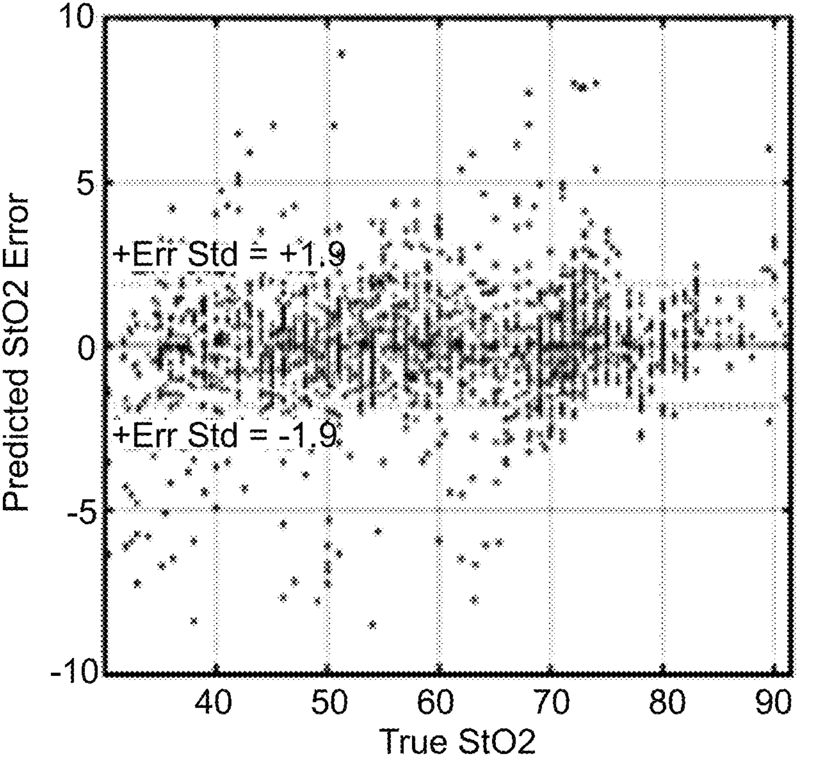
FIGS. 4A-4B are Bland Altman plots comparing gold standard and predicted StO2.
Figure 4B:
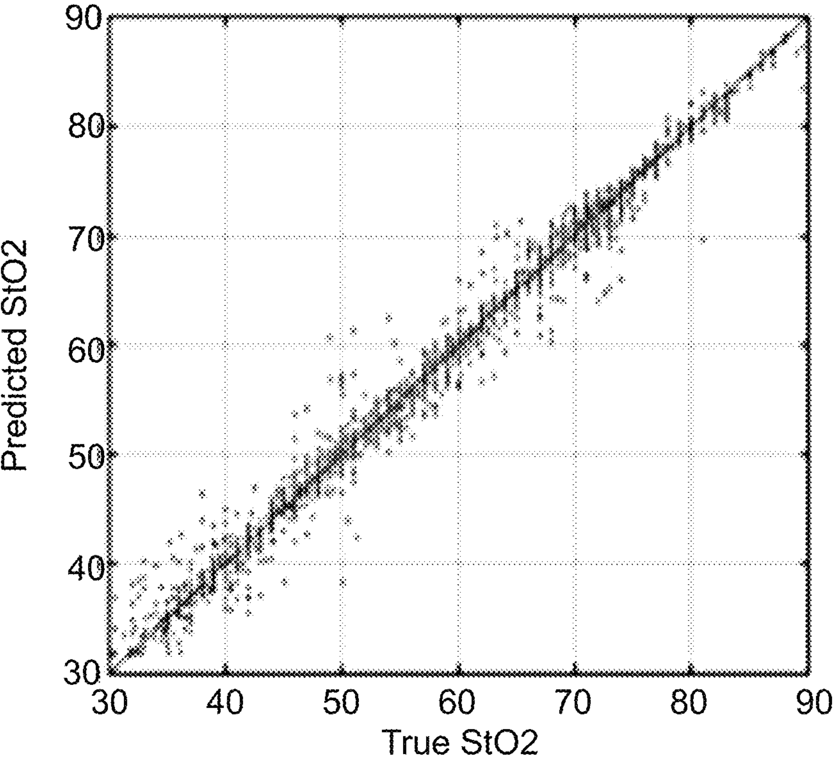

Deoxygenated hemoglobin is more absorptive compared to oxygenated hemoglobin of lights with wavelengths below 805 nm. Oxygenated hemoglobin, however, is more absorptive compared to oxygenated hemoglobin of lights with wavelengths above 805 nm. As tissue oxygenation drops, the normalized reflected intensities for wavelengths below 805 nm decrease, and the normalized reflected intensities for wavelengths above 805 nm increase. The patch was placed on the forearm of six test subjects one on the left arm and once on the right arm. An InSpectra3 device (Hutchinson Corp.) was also placed side by side to capture the gold standard tissue oxygenation value. A pressure cuff was attached to the test subject's arm and was set at 160 mmHg, higher than the test subject's systolic pressure. Towards the end of the experiments, the cuff pressure was released to let arterial blood back into the subjects' palm which consequently increases tissue oxygenation levels. The normalized reflected intensities ($N_i=A_i/A_{805nm}$, $A_i$=reflected intensity of light at $i^{th}$ wavelength index) of the 8 different wavelengths were then given to a neural network regression model to predict a tissue oxygenation value as close as possible to the gold standard tissue oxygenation values. The machine learning neural network predicts the tissue oxygenation values such that |Predicted StO2(t)−Gold standard StO2(t)| is minimized. FIGS. 4A-4B show the Bland Altman plot comparing the gold standard and predicted tissue oxygenation show an average error of 1.9% indicating the model's accuracy.

Testing of Temperature Measurement in Phantoms and Healthy Subjects

Figure 5:
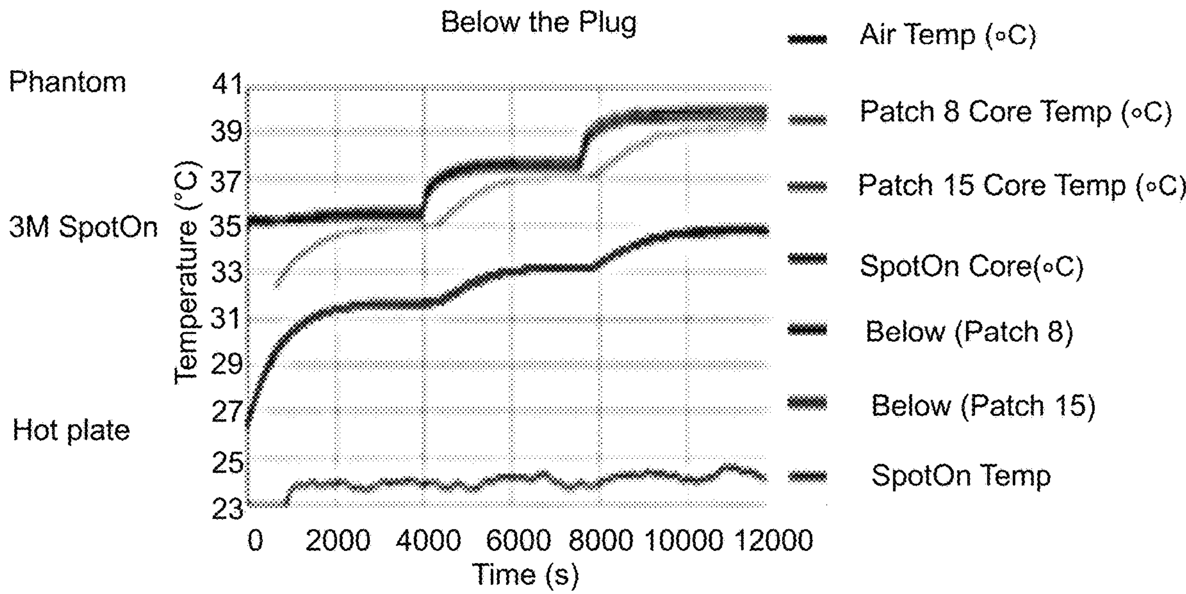
FIG. 5 shows readings from the temperature sensor in the patch due to changes in core temperature over time versus the 3M SPOTON (3M Company, Maplewood, MN).
Figure 6:
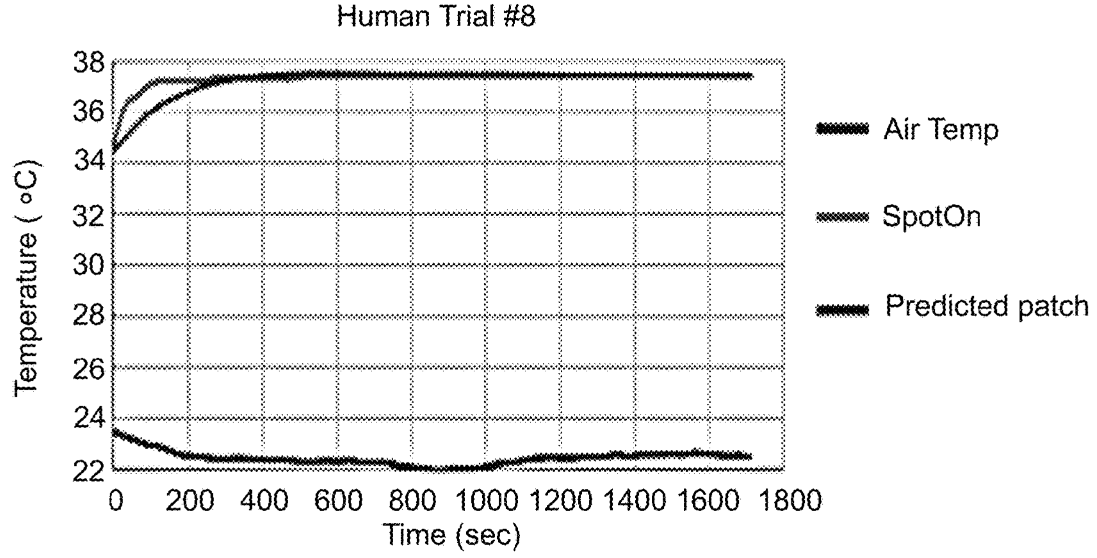
FIG. 6 is a core temperature estimation in a healthy human subject using the temperature sensor in the patch compared to that of the 3M SPOTON.

In vitro a phantom tissue is created with a similar thermal conductivity as the soft tissue of the flap, i.e., the phantom has thermal properties comparable to tissues placed on a hot plate. The phantom tissues are created by adding three layers of Low-Density Polyethylene (LDPE), and Avery MED 3044 double-sided adhesive to stack multiple layers of LDPE together. The thermal conductivity in the phantom tissue is similar to human tissue and calculations can accurately predict how the patches perform on a patient. Raw data (FIG. 5) shows readings from the temperature sensing patch due to changes in core temperature over time vs the 3M SPOTON. The error for the temperature measuring unit in the patches at a steady state was <0.2° C. In vivo tests were carried out on healthy subjects. Representative human subject data is shown in FIG. 6, which shows that the patch can estimate the core temperature comparable to the 3M SPOTON. The dual patch system measures the temperature difference between the reference patch and flap patch at an accuracy of 0.25° C.

Example 2

Musculocutaneous Flap Model in Swine

Animals

A total of 8 adult swine (*Sus scrofa domesticus*, ssp. Large white) with equal numbers of males and females are used to test the dual patch system. For a standard deviation of 20%, a significance level of $\alpha=0.05$, and a power of $1-\beta=0.8$ were applied, resulting in an estimated sample size of 8 animals per group. The swine are provided an environmentally controlled environment where the appropriate temperature, humidity, light cycles, space, hog feed, water, and bedding are all monitored and maintained within established parameters (NIH Guide, Animal Welfare Act, NRC). At all times, strict attention is paid to the management of any pain or distress any animal may be experiencing. The animals are observed daily for general health, pain, and any signs of distress pre- and post-operative.

Generation of Musculocutaneous Flap Model

A porcine musculocutaneous flap model is an established in vivo model for flap monitoring to accurately measure the relative temperature and saline induced edema. Two rectus abdominus myocutaneous flaps are harvested per animal as per the procedure in U.S. Pat. No. 11,857,294, hereby incorporated by reference.

In Vivo Monitoring of StO2, Temperature and Edema

The flap is monitored using a ViOptix device and the flap patch concurrently with arterial and venous clamping. ImpediMed's bioimpedance spectroscopy (BIS) device is used as a benchmark for assessing edema. The animals are monitored for 5 days after the surgery. The flap patch sends the real-time temperature, edema, and tissue oxygenation data to a HIPAA-compliant cloud server. To preserve battery power, the total data collection time required for temperature and tissue oxygenation measurements is <1 minute, but are sent to the server every 15 minutes.

The flap patch is attached to the central portion of the flap along with the Vioptix probe which serves as a control. Both are positioned over the central portion of the flap and are 2-3 cm from each other. Flap perfusion readings are measured at 1-minute intervals for 15 minutes until baseline reading is reached for tissue oxygenation for both the flap patch and the Vioptix probe. A BL connection is established with the flap patch. The ViOptix T.OX (ViOptix, Inc., Newark, California) probe is connected to the external monitor via the fiber optic cable which is attached to the monitor.

Baseline flap readings: A stable reading is taken after 15 minutes and recorded for both the flap patch and the Vioptix probe. Three readings are taken at 5-minute intervals after an initial baseline of 15 min.

Venous congestion experiment: An Acland clamp is applied to the superior epigastric vein and the superior superficial epigastric vein for 15 min. After 15 min the readings on the flap patch and Vioptix T.OX probe are taken, and three readings are taken at 5-minute intervals. After the last reading, the Acland clamp is removed and the flap is left to re-stabilize for 15 min before starting the arterial ischemia experiment.

Arterial ischemia experiment: An Acland clamp is applied to the deep superior epigastric artery for 15 min. Tissue oxygenation measurements are taken after 15 min baseline with the Vioptix T.OX probe and flap patch. Readings are taken every 5 minutes after the 15 min baseline. Three recordings are taken in total every 5 minutes for both the flap patch and the Vioptix T.OX probe. The entire procedure (baseline readings, venous congestion experiment and readings, arterial ischemia experiment and readings) are repeated three times for each flap. After completion, the flap skin is closed to the peripheral wound using resorbable Vicryl sutures and skin staples, and the Vioptix T.OX probe is removed. A surgical dressing is placed on the surgical wound. The flap patch is kept in place and secured for 5 days. The flap patch is securely covered to avoid trauma and contact loss from the underlying skin flap. Measurements are taken every 5 minutes for tissue oxygenation.

REFERENCES

1. Mohan, A. T. & Saint-Cyr, M. Recent Advances in Microsurgery: An Update in the Past 4 Years. *Clin Plast Surg* 47, 663-677 (2020).
2. Bui, D. T. et al. Free flap reexploration: indications, treatment, and outcomes in 1193 free flaps. *Plast Reconstr Surg* 119, 2092-2100 (2007).
3. Hospital and Surgery Costs—Paying for Medical Treatment, debt.org/medical/hospital-surgery-costs.
4. How Much Does a Hospital Stay Cost? PeopleKeep. peoplekeep.com.
5. Papillion, et al. Infrared surface temperature monitoring in the postoperative management of free tissue transfers. The Canadian Journal of Plastic Surgery 17, 97 (2009).
6. Cruz-Segura, et al. Early Detection of Vascular Obstruction in Microvascular Flaps Using a Thermographic Camera. J Reconstr Microsurg 35, 541-548 (2019).
7. Novakovic, et al. Salvage of failed free flaps used in head and neck reconstruction. Head Neck Oncol 1, 33 (2009).

8. Zabaglo, M. and Sharman, T. Postoperative Wound Infection. Clinical Infectious Disease, Second Edition 729-733 (2022).

9. Olsen, et al. Hospital-associated costs due to surgical site infection after breast surgery. Arch Surg 143:53-60 (2008).

What is claimed:

1. A medical patch system for post-operative monitoring of tissue properties in a patient, comprising:

one medical patch positionable on post-operable flap tissue on the patient and another medical patch positionable on adjacent healthy tissue, each of said medical patches comprising:

a first module configured to measure tissue oxygenation; and a second module configured to measure skin temperature;

said medical patch positionable on flap tissue further comprising a third module configured to deliver a therapy effective to accelerate healing of tissue and to stimulate cell proliferation therein; and each of said medical patches comprising a control module configured to:

power the medical patch;

receive wirelessly multimodal time-synchronized data comprising tissue oxygenation and skin temperature data;

calculate a differential physiological parameter ΔStO2 or ΔT or a combination thereof based on the time-synchronized data;

execute an AI algorithm trained to classify a tissue viability state and predict an ischemic risk based on a series of the multimodal time-synchronized data; said tissue viability state and said ischemic risk are determined based on the differential physiological parameter calculated between the medical patch on the flap tissue and the medical patch on the adjacent healthy tissue;

to issue alerts if the ischemic risk exceeds a defined threshold; and adjust dynamically parameters of the therapy delivered by the third module based on said differential physiological parameters.

2. The medical patch of claim 1, wherein the first module comprises a plurality of LEDs that emit wavelengths in a visible spectrum and a near infrared spectrum.

3. The medical patch of claim 1, wherein the second module is further configured to measure ambient temperature.

4. The medical patch of claim 1, wherein the third module delivers a photobiomodulation therapy or an electrical stimulation therapy.

5. The medical patch of claim 4, wherein the third module comprises a plurality of LEDs that emit red light with at least one wavelength of about 600 nm to about 1100 nm effective for a controlled photobiomodulation and a driver circuit.

6. The medical patch of claim 1, wherein the third module comprises a cathode and an anode effective to deliver an electric current of about 0 mA to about 30 mA, a frequence of 0 KHz to about 1 KHz, and duty cycles of 0% to 100% with different shapes to pass through post-operative tissue.

7. The medical patch of claim 1, further comprising a fourth module configured to detect edema in tissue.

8. The medical patch of claim 7, wherein the fourth module comprises another plurality of LEDs that emit light with center wavelengths of about 900 nm to about 1000 nm, of about 1400 nm to about 1500 nm or about 1800 nm to about 2200 nm to detect the edema.

9. A dual patch system for post-operative flap monitoring, comprising:

a flap patch removably attachable to a surgical flap and comprising:

a first tissue oxidation module configured to monitor and measure tissue oxygenation, said tissue oxidation module having a plurality of surface-mounted LEDs that emit at a combination of different wavelengths and a photodetector;

a first thermal sensing module comprising at least one skin-contact temperature sensor; and a therapeutic excitation module comprising a photobiomodulation patch with a driver circuit or a cathode and anode, each of which are configured to accelerate healing and stimulate cell proliferation in the surgical flap;

another patch removably attachable to healthy tissue adjacent to the surgical flap and comprising:

a second tissue oxidation module configured to monitor and measure tissue oxygenation, said tissue oxidation module having a plurality of surface-mounted LEDs that emit at a combination of different wavelengths and a photodetector;

a second thermal sensing module comprising at least one skin-contact temperature sensor and an ambient temperature sensor; and a control module configured to:

power the flap patch and the other patch;

receive wirelessly multimodal time-synchronized data from the flap patch and the other patch comprising tissue oxygenation and skin temperature data;

calculate a differential physiological parameter ΔStO2 or ΔT or a combination thereof based on the time-synchronized data:

execute an AI algorithm trained to classify a tissue viability state and predict an ischemic risk based on a series of the multimodal time-synchronized data from the flap patch; said tissue viability state and said ischemic risk determined based on the differential physiological parameter calculated between the flap patch on the flap tissue and the patch on the healthy tissue adjacent to the flap patch;

issue alerts locally and to a cloud-based dashboard if the ischemic risk exceeds a defined threshold; and adjust dynamically parameters of the therapy delivered by the third module based on said differential physiological parameters.

10. The dual patch system of claim 9, said flap patch and said other patch further comprising an edema detection module that has a plurality of LEDs that emit light with center wavelengths of about 900 nm to about 1000 nm, of about 1400 nm to about 1500 nm or about 1800 nm to about 2200 nm.

11. The dual patch system of claim 9, wherein the plurality of surface-mounted LEDs in the first tissue oxidation module and the second tissue oxidation module emit at 625 nm, 660 nm, 805 nm, and 870 nm.

12. The dual patch system of claim 9, wherein the photobiomodulation patch in the flap patch comprises a plurality of LEDs that emit red light with at least one wavelength of about 600 nm to about 1100 nm effective to control photobiomodulation.

13. The dual patch system of claim 9, wherein the cathode and anode in the flap patch are effective to deliver an electric current of about 0 mA to about 30 mA, a frequence of 0 KHz to about 1 KHz, and duty cycles of 0% to 100% with different shapes to pass through post-operative tissue.

14. The dual patch system of claim 9, wherein the AI algorithm is a deep neural network trained on labeled flap outcome data to predict the probability of flap compromise within a 6-hour horizon.

15. The dual patch system of claim 14, said AI algorithm comprising attention-based temporal filtering configured to weigh recent versus historical measurements in a prediction process.

16. A method for real-time monitoring and modulating tissue health in a surgical flap, comprising the steps of:

placing the flap patch and the other patch of the dual patch system of claim 12 onto the surgical flap and onto the healthy tissue adjacent to the flap patch;

acquiring continuously temperature data and tissue oxygenation data from the flap patch and the other patch;

computing physiological deltas between the surgical flap and the healthy tissue;

inputting multimodal time-series data into an AI algorithm to determine a predicted risk level of tissue viability in the surgical flap;

adjusting automatically parameters of the photobiomodulation patch in the flap patch in response to the predicted risk level; and issuing wireless alerts to a health provider if a deterioration in flap health is detected or predicted.

17. The method of claim 16, wherein the AI algorithm is a deep neural network, the method comprising training the AI algorithm on labeled flap outcome data to predict the probability of flap compromise within a 6-hour horizon, said AI algorithm comprising attention-based temporal filtering configured to weigh recent versus historical measurements in a prediction process.

* * * * *